(12) United States Patent
Zhang

(10) Patent No.: US 11,247,011 B2
(45) Date of Patent: Feb. 15, 2022

(54) PRESSURE CONTROLLER AND TRACHEAL BREATHING TUBE COMPRISING SAME

(71) Applicant: Xialing Zhang, Mountain View, CA (US)

(72) Inventor: Xialing Zhang, Mountain View, CA (US)

( * ) Notice: Subject to any disclaimer, the term of this patent is extended or adjusted under 35 U.S.C. 154(b) by 846 days.

(21) Appl. No.: 16/100,817

(22) Filed: Aug. 10, 2018

(65) Prior Publication Data
US 2019/0192798 A1 Jun. 27, 2019

Related U.S. Application Data

(60) Provisional application No. 62/610,297, filed on Dec. 26, 2017.

(51) Int. Cl.
*A61M 16/04* (2006.01)
*A61M 16/00* (2006.01)
(Continued)

(52) U.S. Cl.
CPC ...... *A61M 16/044* (2013.01); *A61M 16/0003* (2014.02); *A61M 16/208* (2013.01); *A61M 16/209* (2014.02); *A61M 25/1018* (2013.01); *A61M 16/022* (2017.08); *A61M 16/04* (2013.01); *A61M 16/0438* (2014.02); *A61M 16/0465* (2013.01); *A61M 16/0497* (2013.01); *A61M 2016/0027* (2013.01); *A61M 2205/3331* (2013.01); *A61M 2205/583* (2013.01)

(58) Field of Classification Search
CPC .. A61M 16/00; A61M 16/0003; A61M 16/04; A61M 16/0402; A61M 16/0434; A61M 16/044; A61M 16/20; A61M 16/0465; A61M 16/208; A61M 16/209; A61M 2016/0027; A61M 2205/3331; A61M 2205/3334; A61M 2205/583
See application file for complete search history.

(56) References Cited

U.S. PATENT DOCUMENTS 3,985,141 A * 10/1976 Stanley ............... A61M 16/209 128/207.15
4,064,882 A * 12/1977 Johnson ................ A61M 16/04 128/207.15
(Continued)

*Primary Examiner* — Colin W Stuart
(74) *Attorney, Agent, or Firm* — David O. Simmins; IVC Patent Agency

(57) ABSTRACT

Disclosed herein are aspects of a tracheal breathing tube that provides for accurate and reliable control of cannula cuff pressure. Such a tracheal breathing tube include a pressure controller through which a fluid is supplied to a cannula cuff of a tracheal breathing tube and which enables reliable indication of a level of pressure of fluid within the cannula cuff. The pressure controller serves to achieve a proper interface between the cannula cuff and a patient's trachea, thereby addressing important clinical considerations such as anesthesiologist control. Moreover, the pressure controller serves to ensure that proper force is being applied on the patient's tracheal walls by the cannula cuff to thereby limit the potential for post-surgical complications resulting from, for example, inadequate blood supply to an organ or part of the body. swelling of the patient's tracheal walls that can lead to difficulty in breathing, and the like.

18 Claims, 3 Drawing Sheets

(51) Int. Cl.
*A61M 25/10* (2013.01)
*A61M 16/20* (2006.01)

(56) References Cited

U.S. PATENT DOCUMENTS

| | | | | |
|---|---|---|---|---|
| 4,333,452 A * | 6/1982 | Au | ............... | A61M 16/04 |
| | | | | 128/205.24 |
| 4,501,273 A * | 2/1985 | McGinnis | ......... | A61M 16/044 |
| | | | | 128/207.15 |
| 4,825,862 A * | 5/1989 | Sato | ............... | A61M 16/044 |
| | | | | 128/207.15 |
| 4,856,510 A * | 8/1989 | Kowalewski | ....... | A61M 16/044 |
| | | | | 128/207.15 |
| 2011/0152762 A1* | 6/2011 | Hershey | ......... | A61M 25/10184 |
| | | | | 604/99.02 |
| 2014/0196721 A1* | 7/2014 | Gilhuly | ............ | A61M 16/044 |
| | | | | 128/207.15 |
| 2014/0261442 A1* | 9/2014 | Graboi | ............ | A61M 16/044 |
| | | | | 128/207.15 |
| 2014/0261443 A1* | 9/2014 | Lowenstein | ....... | A61M 16/044 |
| | | | | 128/207.15 |
| 2015/0283343 A1* | 10/2015 | Schnell | ............ | A61M 16/044 |
| | | | | 128/207.15 |
| 2015/0314092 A1* | 11/2015 | Kimm | ............ | A61M 16/0479 |
| | | | | 128/207.15 |
| 2019/0009042 A1* | 1/2019 | Bateman | ........... | A61M 16/044 |

\* cited by examiner

PRESSURE CONTROLLER AND TRACHEAL BREATHING TUBE COMPRISING SAME

CROSS-REFERENCE TO RELATED APPLICATIONS

This non-provisional patent application claims priority from U.S. Provisional Patent Application having Ser. No. 62/610,297, filed 26 Dec. 2017, entitled "ADJUSTABLE AIR PRESSURE IN TRACHEAL CANNULA", having a common applicant herewith and being incorporated herein in its entirety by reference.

FIELD OF THE DISCLOSURE

The disclosures made herein relate generally to pressure controllers for fluid delivery apparatuses and, more particularly, to a tracheal breathing tube comprising a cannula cuff pressure controller.

BACKGROUND

It is well known that a medical professional (e.g., a surgeon, nurse, first responder and the like) often has the need to put a tracheal breathing tube into a patient's trachea (i.e., intubation) to help patient breathing. The tracheal breathing tube is a medical device that provides an artificial airway for access to the patient's airway for airway management. An endotracheal tube and a tracheostomy tube are examples of a tracheal breathing tube. The type of tracheal breathing tube is often determined by the type of medical event that the patient is subject to at the time that the need for intubation arises. In an emergency, it is common for an endotracheal tube to be used for such intubation. In cases of longer term care and/or under controlled conditions, it is common for a tracheostomy tube to be used for such intubation.

Placement of a prior art tracheal breathing tube (i.e., a tracheostomy tube 100) is illustrated in FIGS. 1 and 2. As illustrated, a patient 102 has a stoma 104 (opening) leading to his/her trachea 106. A cannula 108 of the tracheostomy tube 100 is inserted into the stoma 104 to provide an artificial airway for the patient 102. The cannula 108 may have a curved portion 110 (e.g., an L shape). A neck flange 112 of the tracheostomy tube 100 may be attached to the neck of the patient 102, for example, using tape and/or straps (not shown). A cannula cuff 114 (also sometimes referred to as an air bag) is located on the outer wall of the cannula 108, and an inflation lumen 116 is located within the wall of the cannula 108 and is connected to the cannula cuff 114. An air valve port 118 is used in combination with the inflation lumen 116 and the cannula cuff 114 such that the cannula cuff 114 may be inflated for creating a fluid (e.g., gas and/or liquid) sealing function between the cannula 108 and the trachea 106 air passage. The air valve port 118 can include a pilot balloon 119 through which a medical professional (e.g., an anesthesiologists) can use fingers to estimate cannula cuff pressure by tactically assessing an inflation level of the pilot balloon 119 and using one's experience to estimate a corresponding inflation level of the cannula cuff 114. The cannula cuff 114 may be inflated with a fluid such as air, although other fluids may such as nitrogen, saline, water, and so forth may be used. The cannula 108 has a connector 120 attached thereto, which is configured to attach the tracheostomy tube 100 to various other tubes and conduits, such as a ventilator tube attached to a ventilator (not shown).

Tracheal breathing tubes are well known to be limited in their ability to accurately and reliably detect and indicate fluid (e.g., air) pressure in a cannula cuff thereof. However, cannula cuff pressure has important clinical considerations such as for anesthesiologist control. Specifically, the cannula cuff pressure needs to be of a sufficient level for the cannula cuff to properly interface with the patient's trachea (i.e., to limit if not inhibit bypassing of fluid). However, excessive cannula cuff pressure can result in undue force being applied on the patient's tracheal walls by the cannula cuff. Such undue force can cause post-use complication such as, for example, ischemia (i.e., inadequate blood supply to an organ or part of the body), swelling of the patient's tracheal walls that can lead to difficulty in breathing, and the like.

Therefore, a tracheal breathing tube that provides for accurate and reliable control of cannula cuff pressure would be advantageous, desirable and useful.

SUMMARY OF THE DISCLOSURE

Embodiments of the present invention are directed to medical devices such as, for example, a tracheal breathing tube that provides for accurate and reliable control of cannula cuff pressure. Embodiments of the present invention are not limited to a particular type of configuration of medical device. A person of ordinary skill in the art will appreciate that the pressure controller disclosed herein can be used with and/or integrated with a multitude of medical devices and other types of devices.

In specific embodiments, the present invention is directed to a valve apparatus through which a fluid (e.g., gas such as air, or nitrogen or liquid such as saline) is supplied to a cannula cuff of a tracheal breathing tube (e.g., an endotracheal tube or a tracheostomy tube) and that enables reliable indication of a level of pressure of such fluid within the cannula cuff. Such a valve apparatus is referred to herein as a cannula cuff pressure controller (i.e., a pressure controller). Such a cannula cuff pressure controller serves to achieve a proper interface between the cannula cuff and a patient's trachea, thereby addressing important clinical considerations such as anesthesiologist control. Moreover, such a cannula cuff pressure controller serves to ensure that proper force is being applied on the patient's tracheal walls by the cannula cuff to thereby limit the potential for post-use complications resulting from, for example, inadequate blood supply to an organ or part of the body, swelling of the patient's tracheal walls that can lead to difficulty in breathing, and the like.

In one embodiment of the present invention, a medical device comprises a tubular body, an inflatable body, an inflation tube, and a pressure controller. The tubular body has a central passage extending between proximate and distal end portions thereof. An inlet is provided at the proximate end portion and an outlet is provided at the distal end portion. The inflatable body is coupled to the tubular body adjacent to the distal end portion thereof. The inflation tube has opposing end portions. A first one of the opposing end portions of the inflation tube is attached to the inflatable body for enabling fluid communication between an interior space of the inflatable body and a central passage of the inflation tube. The pressure controller includes a first fluid flow control structure and a second fluid flow control structure. The first and second fluid flow control structures each include a valve body having a valve chamber therein and a valve assembly within the valve chamber. An interior space of the valve chamber of the first fluid flow control structure is in fluid communication with an inlet of the valve chamber of the second fluid flow control structure. The valve chamber inlet of the second fluid flow control structure is fluidly coupled to a second one of the opposing end portions of the inflation tube for enabling fluid communication between the valve chamber of the first fluid flow control structure and the central passage of the inflation tube. The valve assembly of the first fluid flow control structure provides spring-biased one-way flow control of fluid through the valve chamber thereof. The valve assembly of the second fluid flow control structure provides at least one of spring-biased one-way flow control of fluid through the valve chamber thereof and pressure level visualization of fluid present at the valve chamber inlet of the second fluid flow control structure.

In another embodiment of the present invention, a tracheal breathing tube comprises an outer cannula, a cannula cuff, an inflation tube, and a pressure controller. The outer cannula has a central passage extending between proximate and distal end portions thereof. The cannula cuff is attached to an exterior surface of the outer cannula adjacent to the distal end portion thereof. The inflation tube has a central passage extending between opposing end portions thereof. A first one of the opposing end portions is fluidly coupled to the cannula cuff whereby an interior space of the cannula cuff is in fluid communication with the central passage of the inflation tube. The pressure controller has a main body and a plurality of valve assemblies mounted therein. The main body includes a fluid inlet passage, a fluid outlet passage fluidly coupling the fluid inlet passage, a first valve chamber fluidly coupling the fluid inlet passage and the fluid outlet passage, and a second valve chamber fluidly coupling at least one of the first valve chamber and the fluid outlet passage. The fluid outlet passage is attached to the inflation tube at a second one of the opposing end portions thereof whereby the interior space of the cannula cuff is in fluid communication with the fluid inlet passage of the main body. A first one of the valve assemblies is provided within the first valve chamber and a second one of the valve assemblies is provided within the second valve chamber. The first one of the valve assemblies includes a first sealing member that is spring biased to provide one-way flow control of fluid from the fluid inlet into the first valve chamber. The second one of the valve assemblies includes a second sealing member that is spring biased for inhibiting unrestricted fluid flow from the first valve chamber into the second valve chamber. The second valve assembly includes a pressure level indicating portion that provides a visual indication of the fluid pressurization within the interior space of the cannula cuff as a function of the displacement of the second sealing member.

In another embodiment of the present invention, a tracheal breathing tube comprises an outer cannula, a cannula cuff, an inflation tube, and a pressure controller. The outer cannula has a central passage extending between proximate and distal end portions thereof. The cannula cuff is attached to an exterior surface of the outer cannula adjacent to the distal end portion thereof. The inflation tube has a central passage extending between opposing end portions thereof. A first one of the opposing end portions is fluidly coupled to the cannula cuff whereby an interior space of the cannula cuff is in fluid communication with the central passage of the inflation tube. The pressure controller includes a main body having a first valve chamber and a second valve chamber. The first valve chamber defines a fluid inlet passage of the main body and a fluid outlet passage of the main body that is coupled to the fluid inlet passage. The fluid outlet passage is attached to the inflation tube at a second one of the opposing end portions thereof whereby the interior space of the cannula cuff is in fluid communication with the fluid inlet passage of the main body. A first valve assembly provided within the first valve chamber includes a first sealing member spring-biased to a seated position within the first valve chamber such that pressurized fluid provided at the fluid inlet passage of the main body at a pressure sufficient to overcome a force of the spring-bias of the first sealing member causes displacement of the first sealing member and flow of the pressurized fluid into the first valve chamber whereby fluid pressurization occurs within the interior space of the cannula cuff. A second valve assembly provided within the second valve chamber includes a second sealing member spring-biased to a seated position within the second valve chamber to close a fluid inlet passage of the second valve chamber. The fluid inlet passage of the second valve chamber is in fluid communication with the fluid outlet passage of the main body such that the fluid pressurization within the interior space of the cannula cuff causes displacement of the second sealing member proportional to a force of the spring-bias of the second sealing member. The second valve assembly includes a pressure level indicating portion that provides a visual indication of a level of the fluid pressurization within the interior space of the cannula cuff These and other objects, embodiments, advantages and/or distinctions of the present invention will become readily apparent upon further review of the following specification, associated drawings and appended claims.

DETAILED DESCRIPTION

Figure 1:
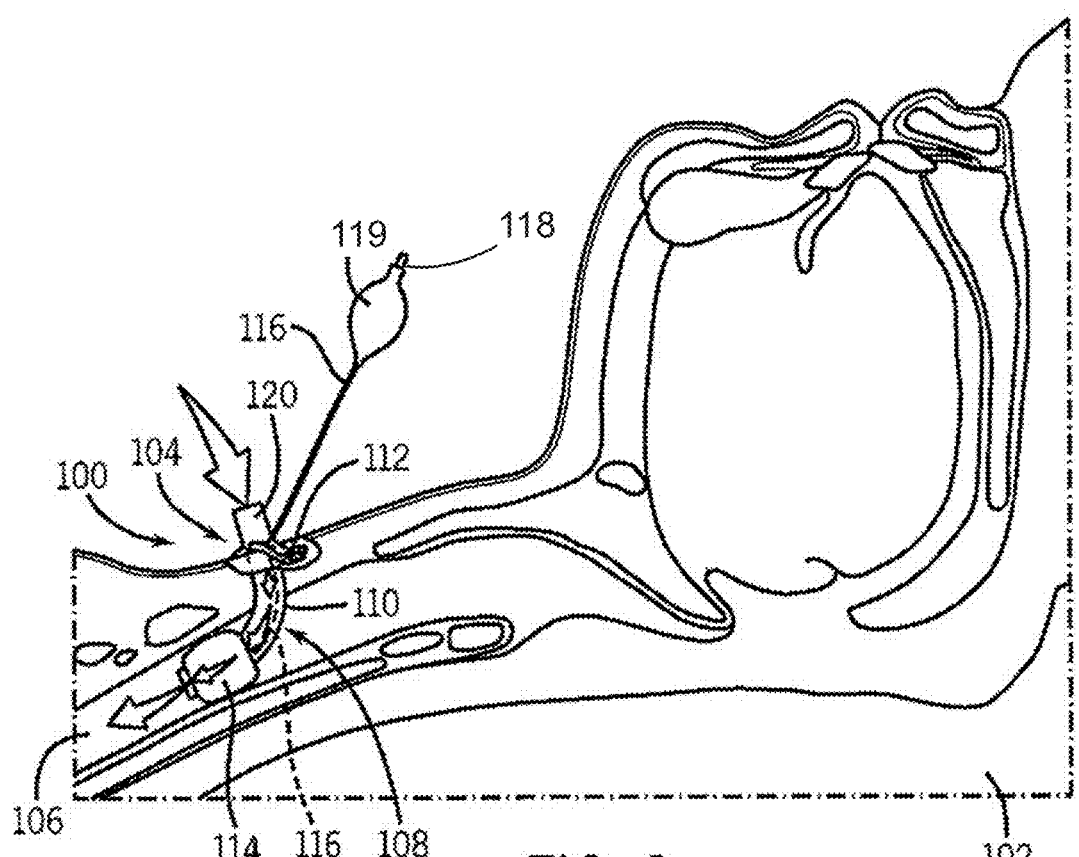
FIG. 1 is a diagrammatic view showing placement of a prior art tracheal breathing tube.
Figure 2:
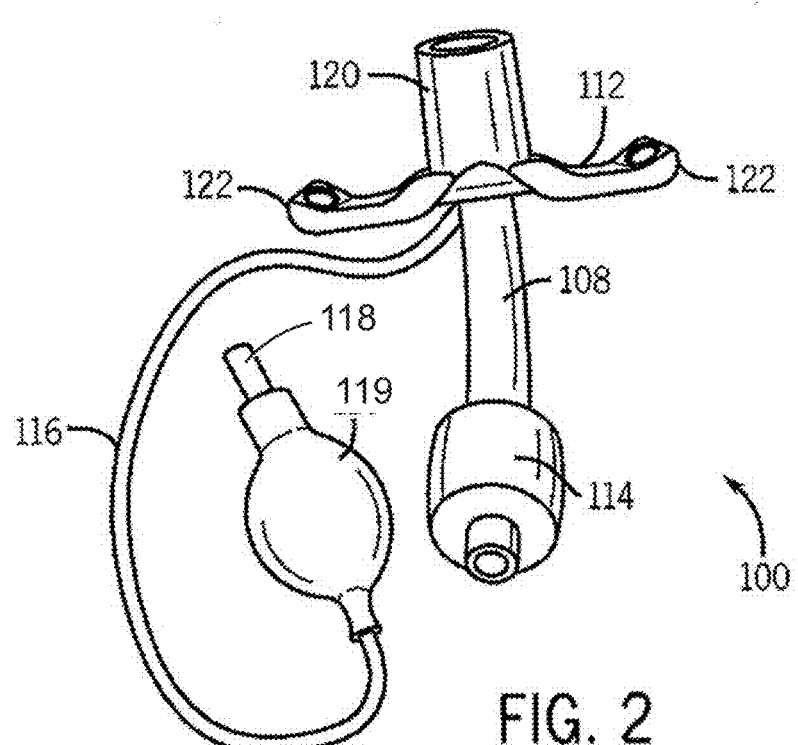
FIG. 2 is a diagrammatic view showing construction of the prior art tracheal breathing tube of FIG. 1.
Figure 3:
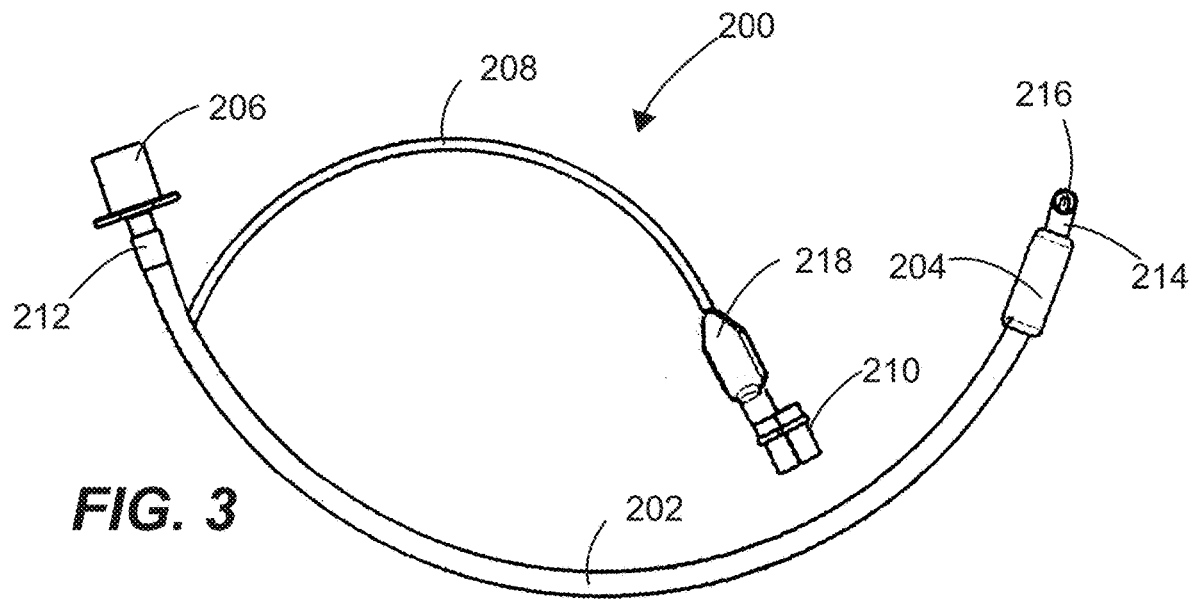
FIG. 3 is a diagrammatic view showing an endotracheal tube in accordance with an embodiment of the present invention.
Figure 4:
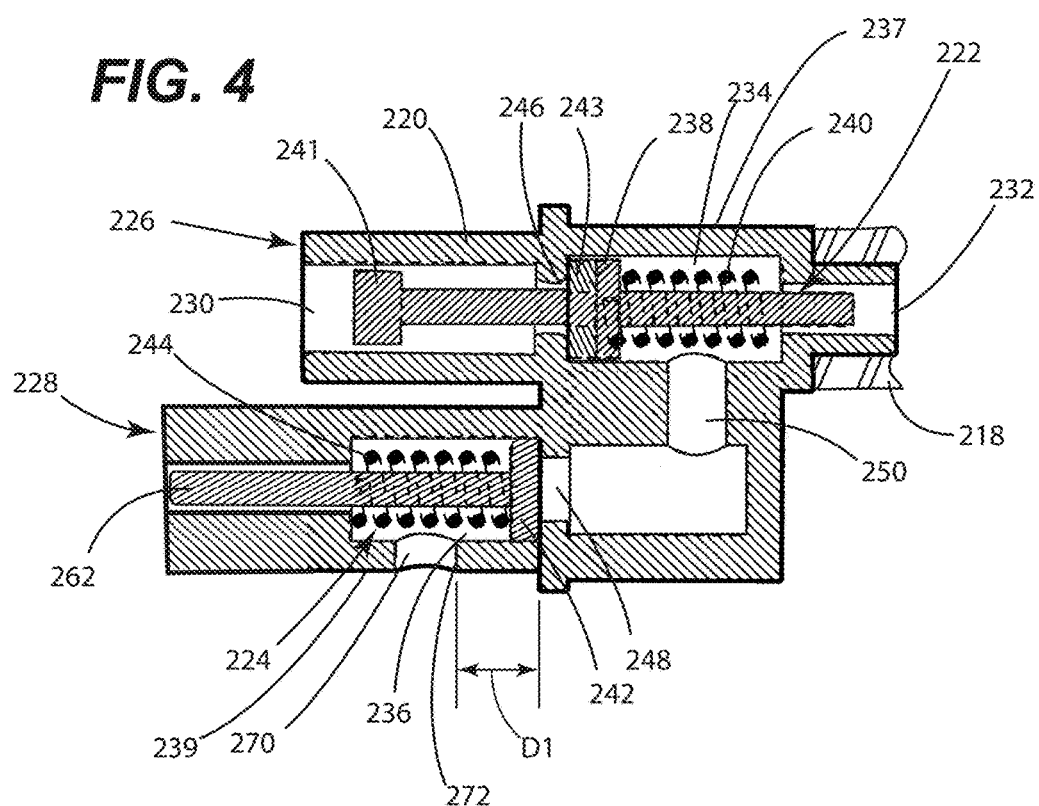
FIG. 4 is a cross-sectional view of a pressure controller in accordance with a first embodiment of the present invention.
Figure 5:
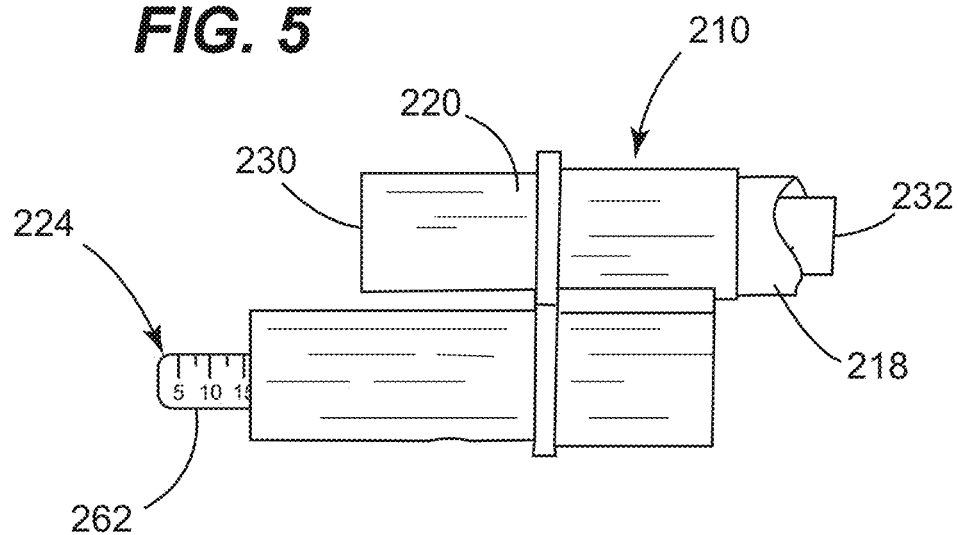
FIG. 5 is a diagrammatic view of the pressure controller shown in FIG. 4.

FIGS. 3-5 show various aspects of an endotracheal tube 200 configured in accordance with an embodiment of the present invention. The endotracheal tube 200, which is an example of a medical device, provides for accurate and reliable control of cannula cuff pressure thereby enabling a proper interface (i.e., based on a patient's particular requirements/condition) between the cannula cuff and a patient's trachea to be achieved. Such accurate and reliable control of cannula cuff pressure is beneficial to important clinical considerations such as anesthesiologist control because it ensures that proper force is being applied on the patient's tracheal walls by the cannula cuff. In doing so, this limits the potential for post-surgical complications resulting from, for example, inadequate blood supply to an organ or part of the body, swelling of the patient's tracheal walls that can lead to difficulty in breathing, and the like.

The endotracheal tube 200 is one example of a tracheal breathing tube configured in accordance with an embodiment of the present invention. Embodiments of the present invention can similarly be configured as a tracheostomy tube. Whereas an endotracheal tube is placed in a patient though the mouth, a tracheostomy tube is placed through an opening in a patient's throat (i.e., a stoma).

The endotracheal tube 200 includes an outer cannula 202 (i.e., a tubular body), a cannula cuff 204, a connector 206, an inflation tube 208, and a pressure controller 210. The outer cannula 202 may be the only cannula (i.e., the cannula) or, optionally, an inner cannula (not shown) may be disposed within a central passage of the outer cannula 202. The outer cannula 202 has a proximate end portion 212 and a distal end portion 214. A central passage 216 extends through the outer cannula 202 between the proximate and distal end portions 212, 214. The cannula cuff 204 (i.e., an inflatable body) is attached to an exterior surface of the outer cannula 202 adjacent to the distal end portion 214. As shown, the cannula cuff 204 can have a central opening with the distal end portion 214 of the outer cannula 202 extending through the central opening. The connector 206, which is used for allowing the endotracheal tube 200 to be connected to various other tubes and conduits (e.g., a ventilator tube), is attached to the outer cannula at the proximate end 212. The inflation tube 208 has a central passage extending between opposing end portions thereof. A first one of the opposing end portions of the inflation tube 208 (i.e., a first end portion) is fluidly coupled to the cannula cuff 204 whereby an interior space of the cannula cuff 204 is in fluid communication with the central passage of the inflation tube 208. A second one of the opposing end portions of the inflation tube 208 (i.e., a second end portion) is attached to the pressure controller 210.

A fluid such as water, saline, air or nitrogen is supplied under pressure to the cannula cuff 204 via the pressure controller 210 for inflating the cannula cuff 204 to provide a fluid sealing interface between the outer cannula 202 and the patient's tracheal air passage. The pressure control 210 provides for accurate and reliable control of cannula cuff pressure as it relates to pressure that is exerted by the cannula cuff 204 on the walls of the patient's trachea. Optionally, as best shown in FIG. 3, a pilot balloon 218 can be fluidly coupled between the inflation tube 208 and the pressure controller 210 for allowing tactile assessment of the pressure within the cannula cuff 204. It is disclosed herein that the pilot balloon 218 can be omitted and the inflation tube 208 can be attached directly to the pressure controller 210.

Referring now to FIGS. 4 and 5, the pressure controller 210 is discussed in greater detail. In accordance with embodiments of the present invention, the pressure controller 210 is used for delivering pressurized fluid (i.e., a gas or a liquid) to the cannula cuff 204 for inflating the cannula cuff 204 and for maintaining such fluid at a desired level of pressure to achieve a preferred level of force being exerted on the walls of a patient's trachea. To this end, in preferred embodiments, the pressure controller 210 is configured to provide a visual indication of a level of fluid pressure within the cannula cuff 204, to maintain fluid pressure at given level (e.g., 12 mmHg-15 mmHg), and to inhibit pressure within the cannula cuff 204 from exceeding a maximum inflation pressure. Such visual indication preferably includes visually depicting a quantitative fluid pressure level (e.g., a gauge with incremental pressure levels) and/or a qualitative level of fluid pressure.

The pressure controller 210 includes a main body 220 and a plurality of valve assemblies (i.e., first valve assembly 222 and second valve assembly 224). The main body 220 includes a fluid inlet passage 230, a fluid outlet passage 232, a first valve chamber 234, and a second valve chamber 236. The first valve assembly 222 is located within the first valve chamber 234 and the second valve assembly 224 is located within the second valve chamber 236. The first valve assembly 222 includes a first sealing member 238 and a first biasing spring 240. The first valve assembly 222 can include a structure 241 for allowing manual displacement of the first sealing member 238 for enabling depressurization of the first and second valve chambers 234, 236 (e.g., by allowing pressurized fluid from escaping via the inlet passage 230). The second valve assembly 224 includes a second sealing member 242 and a second biasing spring 244. Such biasing springs 238, 240 are examples of resilient members that provide a spring biasing force on the respective one of the sealing members 238, 242. The valve assemblies 222, 224 and the main body 220 are jointly configured such that the sealing members 238, 242 are spring-biased to a respective seated position for closing an inlet 246, 248 into the interior space of the respective one of the valve chambers 234, 236. When in a seated position (shown), the first sealing member 238 provides a fluid-tight seal preventing flow of fluid through the inlet 246 of the first valve chamber 234. When not in the seated position, the first sealing member 238 permits the flow of fluid past the sealing member 238 through a space between the sealing member 238 and a cylindrical wall of the main body 220 within which the sealing member 238 resides. The second sealing member 242 provides or enables a fluid-tight seal with a respective valve chamber surface (i.e., cylindrical surface) of the main body 220 for enabling pressure to be contained within the second valve chamber 236 as the second sealing member 242 moved between a seated position (shown) and displaced positions. One or both of the sealing members 238, 242 can include a resilient sealing structure (e.g., resilient sealing structure 243) that serves to provide the fluid-tight seal with a mating surface of the main body 220. An O-ring and a polymeric gasket are examples of the resilient sealing structure. A resilient sealing structure of the first sealing member 238 would provide a seal between the wall through which the inlet 246 extends when the first sealing member 238 is in the seated position. A resilient sealing structure of the second sealing member 242 would provide a seal between the cylindrical wall that defines the space within which the second sealing member 242 resides.

As best shown in FIG. 4, each of the valve assemblies 222, 224 (i.e., the first and second valve assemblies) and the portion of the main body 220 comprising the respective valve chamber 234, 236 (i.e., the first and second valve chambers) in which a particular one of the valve assemblies 222, 224 is disposed jointly form a respective fluid flow control structure (i.e., a first fluid flow control structure 237 and a second fluid flow control structure 239). The portion of the main body 220 comprising the respective one of the valve chambers 234, 236 in which each of the valve assemblies 222, 224 is disposed is also referred to herein as a valve body. Although the pressure controller 210 is shown with both valve bodies being part of a one-piece main body structure, in some embodiments of the present invention, the valve assemblies 222, 224 can be disposed in separate valve bodies that are attached via an attachment structure such as a pressure transfer conduit.

The fluid outlet passage 232 is fluidly coupled to the fluid inlet passage 230 via the first valve chamber 234. In preferred embodiments (shown), the second valve chamber 236 is fluidly coupled directly to the first valve chamber 234 via a pressure transfer passage 250. Optionally, the second valve chamber 236 can be fluidly coupled to the first valve chamber 234 through the fluid outlet passage 232. The inflation tube 208 is fluidly coupled between the fluid outlet passage 232 and the cannula cuff 204 whereby the interior space of the cannula cuff 204 is in fluid communication with the first valve chamber 234. In this respect, the pressure of fluid within the first valve chamber 234, the second valve chamber 236, the fluid outlet passage 232 and the interior space of the cannula cuff 204 are substantially the same when a pressurized supply of fluid being provided at the inlet passage 230.

To unseat a respective one of the sealing members 238, 242 for allowing flow of a fluid into a respective one of the valve chambers 234, 236, a fluid pressure exerted on the face of a respective one of the sealing members 238, 242 must be greater than a resulting force that exceeds a preload force of the respective one of the biasing springs 240, 244. The preload force of the respective one of the springs 240, 244 when the respective one of the sealing members 238, 242 is in the seated position is a static spring-bias force (i.e., force resulting from compression of spring when sealing member is in the seated position). Displacement of a respective one of the sealing members 238, 242 from its seated position to a displaced position further compresses the respective one of the springs 240, 244 thereby generating a dynamic spring-bias force (i.e., additional force resulting from further compression of the spring when the sealing member is displaced from its seated position). The static and dynamic spring-bias forces are proportional to an elastic coefficient of the second biasing spring 244.

In view of fluid communication between the fluid inlet passage 248 of the second valve chamber 236 and the fluid outlet passage 232, fluid pressurization within the interior space of the cannula cuff 204 of a sufficient level causes displacement of the second sealing member 242 to be proportional to a force of the spring-bias of the second sealing member 242. The second valve assembly 224 provides spring-biased one-way flow control of fluid through the first valve chamber 234 and provides pressure level visualization of fluid within the valve chambers 234, 236. As discussed above, the fluid pressure level at the valve chamber inlet 248 of the second valve chamber 236 is effectively, if not identically, the same as the fluid pressure level within the valve chambers 234, 236 and the interior space of the cannula cuff 204.

Still referring to FIGS. 4 and 5, for providing pressure level visualization of fluid present at the valve chamber inlet 248, the second valve assembly 224 can include a pressure level indicating portion that provides a visual indication of a level of the fluid pressurization within the interior space of the cannula cuff 204. The pressure indicating portion visually indicates a quantitative or qualitative level of pressure within the interior space of the cannula cuff 204. As shown, a quantitative level of fluid pressure can be a numeric indication of pressure (numeric scale) corresponding to the spring-bias force resulting from displacement of the second sealing member 242. The quantitative level of fluid pressure can be visually read from a scale provided on a gauge member 262 of the second valve assembly 224 that extends from the main body 220 (i.e., due to displacement of the second sealing member 242) by a distance proportional to fluid pressure within the interior space of the cannula cuff 204.

As shown in FIG. 4, the main body 220 can include an aperture 270 that extends between an interior space of the second valve chamber 236 and an exterior surface of the main body 220. A leading edge 272 of the aperture 270 is located a first distance D1 from the inlet 248 of the second valve chamber 236. The second sealing member 242 and the second valve chamber 236 are jointly configured whereby fluid pressure within the second valve chamber 236 is maintained until the second sealing member 242 is displaced from its seated position by a distance equal to the first distance D1. Such joint configuration can be that of a piston (i.e., the second sealing member 242) within a cylinder (i.e., an interior surface of the second valve chamber 236). In this respect, the aperture 270 serves as a pressure bleeding structure that provides for fluid from within the second valve chamber 236 to be released to an environment external to the main body 220 when the second sealing member 242 is sufficiently displaced from its seated position due to a fluid pressure at the inlet 248 of the second valve chamber 236 being above a maximum fluid pressure within the interior space of the cannula cuff 204. This pressure bleeding functionality inhibits fluid within the interior space of the cannula cuff 204 from exceeding a pressure that would adversely impact force applied to the trachea of a patient. Such applied force is proportional to the force required for displacing the second sealing member from its seated position to the first distance D1. A recess forming a channel within a surface of the second valve chamber is another example of a pressure bleeding structure that can be used for providing the pressure bleeding functionality.

It is disclosed herein that embodiments of a pressure controller in accordance with the present invention can be configured whereby the static spring bias force is adjustable. Such adjustment would result in the ability to adjust the level of pressure within the interior space of the cannula cuff 204 required for causing displacement of the second sealing member 242 and thus the level of pressure within the interior space of the cannula cuff 204 required for causing the disclosed pressure bleeding functionality. Examples of such adjustment include replacement for the second biasing spring 244 with a spring of different elastic coefficient (i.e., different spring rate), a movable control member that allows the static spring bias force for a given second biasing spring to be selectively adjusted, and the like.

Figure 6:
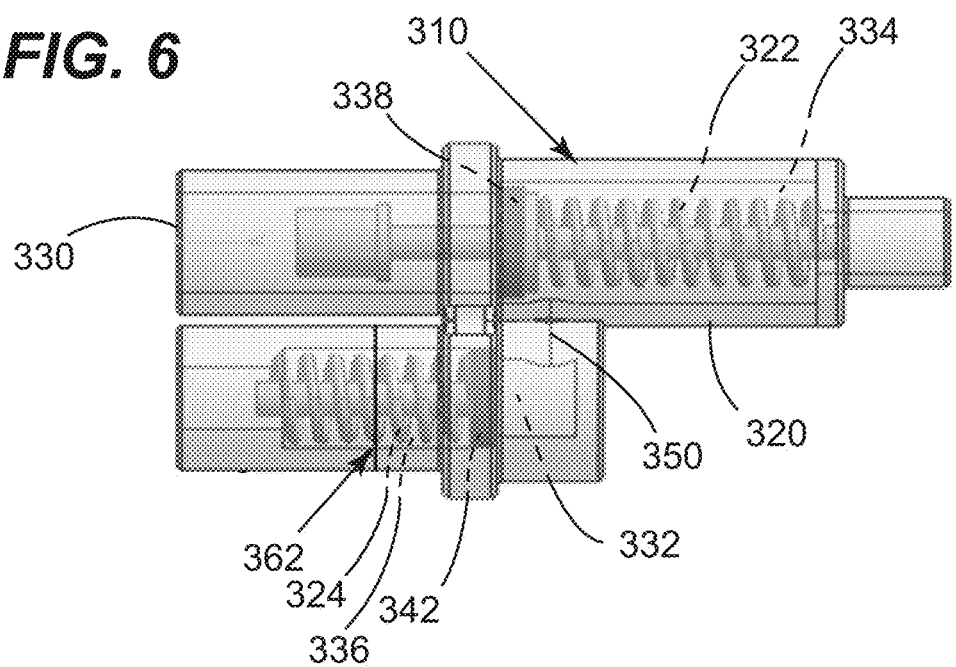
FIG. 6 is a diagrammatic view of a pressure controller in accordance with a second embodiment of the present invention.

A pressure controller 310 configured in accordance with another embodiment of the present invention is shown in FIG. 6. The pressure controller 310 includes an internal structure functionally comparable to that of the pressure controller 210 discussed above. For example, the pressure controller 310 can have a first sealing member 338 of a first valve assembly 322 and a second sealing member 342 of a second valve assembly 324 that each provide or enable a fluid-tight seal with a respective valve chamber surface of a main body 320. Source pressure at inlet 330 causes movement of the first valve assembly 322 to the right thereby allowing air pressure into the first valve chamber 334 and into the fluid outlet passage 332. A pressure transfer passage 350 between the first valve chamber 334 and the second valve chamber 336 allows pressure within the first valve chamber 334 to be exposed within the second valve chamber 336. Such exposure of the pressure within the second valve chamber 336 causes a corresponding movement of the second valve assembly 324 to the left.

As shown, a qualitative level of fluid pressure can be a relative indication of pressure such one or more pressure level indication lines 362 or other indicia indicating a level of fluid pressure or range of fluid pressure that is acceptable and unacceptable. The main housing 320 can be made from a see-through (e.g., made from a transparent or translucent material) through which a position of the second sealing member 342 can be seen by the unaided eye thereby allowing a displaced position of the second sealing member 342 of the second valve assembly 324 to be visualized relative to indicia provided on the main body 320. Such indicia provided on the main body 320 can be a scale indicating quantitative pressure level, one or more lines indicating a qualitative range acceptable pressure levels, a color-coded range of positions of the second sealing member 342 corresponding to acceptable and unacceptable pressure within the interior space of a cannula cuff fluidly coupled to the pressure controller 310, and the like.

In use, a tracheal breathing tube in accordance with the present invention is inserted into the airway of a patient. Pressurized air is supplied to the pressure controller of the tracheal breathing tube. A user uses visual pressure indication of the pressure controller to determine when a desired degree of inflation of the cannula cuff is achieved and to ensure that the cannula cuff is not over-inflated.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A medical device, comprising:
    a tubular body having a central passage extending between proximate and distal end portions thereof, wherein an inlet is provided at the proximate end portion and an outlet is provided at the distal end portion;
    an inflatable body coupled to the tubular body adjacent to the distal end portion thereof;
    an inflation tube having opposing end portions, wherein a first one of the opposing end portions of the inflation tube is attached to the inflatable body for enabling fluid communication between an interior space of the inflatable body and a central passage of the inflation tube; and
    a pressure controller including a first fluid flow control structure and a second fluid flow control structure, wherein the first and second fluid flow control structures each include a valve body having a valve chamber therein and a valve assembly within the valve chamber, wherein an interior space of the valve chamber of the first fluid flow control structure is in fluid communication with an inlet of the valve chamber of the second fluid flow control structure, wherein said valve chamber inlet of the second fluid flow control structure is fluidly coupled to a second one of the opposing end portions of the inflation tube for enabling fluid communication between the valve chamber of the second fluid flow control structure and the central passage of the inflation tube, wherein the valve assembly of the first fluid flow control structure provides spring-biased one-way flow control of fluid through the valve chamber thereof, and wherein the valve assembly of the second fluid flow control structure provides at least one of spring-biased one-way flow control of fluid through the valve chamber thereof and pressure level visualization of fluid present at said valve chamber inlet of the second fluid flow control structure;
    wherein:
        said spring-biasing of the second fluid flow control structure urges a sealing member of the second fluid flow control structure into a seated position at which the sealing member closes the inlet of the valve chamber thereof;
        a pressure level indicating portion includes a gauge member one of attached to and integral with the sealing member thereof; and
        the gauge member extends from the valve body of the second fluid flow control structure when the sealing member thereof is displaced from the seated position.

2. The medical device of claim 1 wherein the pressure level indicating portion that provides a visual indication of fluid pressurization at said valve chamber inlet of the second fluid flow control structure.

3. A medical device, comprising:
    a tubular body having a central passage extending between proximate and distal end portions thereof, wherein an inlet is provided at the proximate end portion and an outlet is provided at the distal end portion;
    an inflatable body coupled to the tubular body adjacent to the distal end portion thereof;
    an inflation tube having opposing end portions, wherein a first one of the opposing end portions of the inflation tube is attached to the inflatable body for enabling fluid communication between an interior space of the inflatable body and a central passage of the inflation tube; and
    a pressure controller including a first fluid flow control structure and a second fluid flow control structure, wherein the first and second fluid flow control structures each include a valve body having a valve chamber therein and a valve assembly within the valve chamber, wherein an interior space of the valve chamber of the first fluid flow control structure is in fluid communication with an inlet of the valve chamber of the second fluid flow control structure, wherein said valve chamber inlet of the second fluid flow control structure is fluidly coupled to a second one of the opposing end portions of the inflation tube for enabling fluid communication between the valve chamber of the second fluid flow control structure and the central passage of the inflation tube, wherein the valve assembly of the first fluid flow control structure provides spring-biased one-way flow control of fluid through the valve chamber thereof, and wherein the valve assembly of the second fluid flow control structure provides at least one of spring-biased one-way flow control of fluid through the valve chamber thereof and pressure level visualization of fluid present at said valve chamber inlet of the second fluid flow control structure, wherein the valve chamber of the second fluid flow control structure includes a pressure bleeding structure through which fluid from within the valve chamber of the first fluid flow control structure is released in response to a sealing member of the valve assembly of the second fluid flow control structure being displaced from a seated position thereof when subjected to a fluid pressure at the inlet of the valve chamber of the second fluid flow control structure that is above a maximum inflatable body pressure, wherein the second one of the opposing end portions of the inflation tube is coupled to said valve chamber inlet of the second fluid flow control structure through the valve chamber of the first fluid flow control structure.

4. The medical device of claim 3 wherein:
the pressure bleeding structure includes one of a recess and an aperture exposed within a surface of the valve chamber in which the valve assembly of the second fluid flow control structure is disposed;
a leading edge of the pressure bleeding structure is located a first distance from the inlet of the valve chamber of the second fluid flow control structure; and
the sealing member of the valve assembly of the second fluid flow control structure and the valve chamber of the second fluid flow control structure are jointly configured whereby fluid pressure is maintained within the valve chamber of the first second fluid flow control structure until the sealing member is displaced from the seated position by a distance equal to the first distance.

5. The medical device of claim 4 wherein:
the second fluid flow control structure includes a pressure level indicating portion including a gauge member one of attached to and integral with the sealing member thereof;
the gauge member extends from the valve body of the second fluid flow control structure when the sealing member thereof is displaced from the seated position;
the gauge member extends from the valve body of the second fluid flow control structure by a prescribed maximum distance when the maximum inflatable body pressure is exhibited at the inlet of the second fluid flow control structure; and
the first distance corresponds to the prescribed maximum distance.

6. A medical device, comprising:
a tubular body having a central passage extending between proximate and distal end portions thereof, wherein an inlet is provided at the proximate end portion and an outlet is provided at the distal end portion;
an inflatable body coupled to the tubular body adjacent to the distal end portion thereof;
an inflation tube having opposing end portions, wherein a first one of the opposing end portions of the inflation tube is attached to the inflatable body for enabling fluid communication between an interior space of the inflatable body and a central passage of the inflation tube; and
a pressure controller including a first fluid flow control structure and a second fluid flow control structure, wherein the first and second fluid flow control structures each include a valve body having a valve chamber therein and a valve assembly within the valve chamber, wherein an interior space of the valve chamber of the first fluid flow control structure is in fluid communication with an inlet of the valve chamber of the second fluid flow control structure, wherein said valve chamber inlet of the second fluid flow control structure is fluidly coupled to a second one of the opposing end portions of the inflation tube for enabling fluid communication between the valve chamber of the second fluid flow control structure and the central passage of the inflation tube, wherein the valve assembly of the first fluid flow control structure provides spring-biased one-way flow control of fluid through the valve chamber thereof, wherein the valve assembly of the second fluid flow control structure provides at least one of spring- biased one-way flow control of fluid through the valve chamber thereof and pressure level visualization of fluid present at said valve chamber inlet of the second fluid flow control structure, and wherein the valve chamber of the second fluid flow control structure includes a pressure bleeding structure through which fluid from within the valve chamber of the first fluid flow control structure is released in response to a sealing member of the second one of the valve assemblies being displaced from a seated position thereof when subjected to a fluid pressure at the inlet of the valve chamber of the second fluid flow control structure that is above a maximum inflatable body pressure.

7. The medical device of claim 6 wherein:
said spring-biasing of the second fluid flow control structure urges the sealing member of the second fluid flow control structure into the seated position at which the sealing member closes the inlet of the valve chamber thereof;
a pressure level indicating portion includes a gauge member one of attached to and integral with the sealing member thereof; and
the gauge member extends from the valve body of the second fluid flow control structure when the sealing member thereof is displaced from the seated position.

8. The medical device of claim 6 wherein:
the tubular body is an outer cannula;
the inflatable body is a cannula cuff having a central opening; and
the distal end portion of the outer cannula extends through the central opening.

9. The medical device of claim 6 wherein:
the pressure bleeding structure includes one of a recess and an aperture exposed within a surface of the valve chamber in which the valve assembly of the second fluid flow control structure is disposed;
a leading edge of the pressure bleeding structure is located a first distance from the inlet of the valve chamber of the second fluid flow control structure; and
the sealing member of the valve assembly of the second fluid flow control structure and the valve chamber of the second fluid flow control structure are jointly configured whereby fluid pressure is maintained within the valve chamber of the first fluid flow control structure until the sealing member is displaced from the seated position by a distance equal to the first distance.

10. The medical device of claim 9 wherein displacement of the sealing member from the seated position to the first distance is achieved when the maximum inflatable body pressure is exhibited at the inlet of the second fluid flow control structure.

11. A tracheal breathing tube, comprising:
an outer cannula having a central passage extending between proximate and distal end portions thereof;
a cannula cuff attached to an exterior surface of the outer cannula adjacent to the distal end portion thereof;
an inflation tube having a central passage extending between opposing end portions thereof, wherein a first one of the opposing end portions is fluidly coupled to the cannula cuff whereby an interior space of the cannula cuff is in fluid communication with the central passage of the inflation tube; and
a pressure controller having a main body and a plurality of valve assemblies mounted therein, wherein the main body includes a fluid inlet passage, a fluid outlet passage fluidly coupling the fluid inlet passage, a first valve chamber fluidly coupling the fluid inlet passage and the fluid outlet passage and a second valve chamber fluidly coupling to at least one of the first valve chamber and the fluid outlet passage, wherein the fluid outlet passage is attached to the inflation tube at a second one of the opposing end portions thereof whereby the interior space of the cannula cuff is in fluid communication with the fluid inlet passage of the main body, wherein a first one of the valve assemblies is provided within the first valve chamber and a second one of the valve assemblies is provided within the second valve chamber, wherein the first one of the valve assemblies includes a first sealing member that is spring biased to provide one-way flow control of fluid from the fluid inlet passage, wherein the second one of the valve assemblies includes a second sealing member that is spring biased for inhibiting unrestricted fluid flow from the first valve chamber into the second valve chamber, and wherein the second valve assembly includes a pressure level indicating portion that provides a visual indication of fluid pressurization within the interior space of the cannula cuff as a function of displacement of the second sealing member.

12. The tracheal breathing tube of claim 11 wherein the second valve chamber includes a pressure bleeding structure through which fluid from within the first valve chamber is released in response to the second sealing member being displaced from a seated position thereof when fluid pressure within the interior space of the cannula cuff is above a maximum cannula cuff pressure.

13. The tracheal breathing tube of claim 12 wherein:
the pressure bleeding structure includes one of a recess and an aperture exposed within a surface of the second valve chamber;
a leading edge of the pressure bleeding structure is located a first distance from an inlet of the second valve chamber; and
the sealing member of the second one of the valve assemblies and the second valve chamber are jointly configured whereby fluid pressure is maintained within the first valve chamber until the sealing member of the second one of the valve assemblies is displaced from the seated position by a distance equal to the first distance.

14. The tracheal breathing tube of claim 11 wherein:
the pressure level indicating portion includes a gauge member one of attached to and integral with the second sealing member;
the gauge member extends from the main body when the second sealing member is displaced from a seated position thereof; and
the gauge member extends from the main body by a prescribed maximum distance when a maximum cannula cuff pressure is exhibited at an inlet of the second valve chamber.

15. A tracheal breathing tube, comprising:
an outer cannula having a central passage extending between proximate and distal end portions thereof;
a cannula cuff attached to an exterior surface of the outer cannula adjacent to the distal end portion thereof;
an inflation tube having a central passage extending between opposing end portions thereof, wherein a first one of the opposing end portions is fluidly coupled to the cannula cuff whereby an interior space of the cannula cuff is in fluid communication with the central passage of the inflation tube; and
a pressure controller including a main body having a first valve chamber and a second valve chamber, wherein the first valve chamber defines a fluid inlet passage of the main body and a fluid outlet passage of the main body that is coupled to the fluid inlet passage, wherein the fluid outlet passage is attached to the inflation tube at a second one of the opposing end portions thereof whereby the interior space of the cannula cuff is in fluid communication with the fluid inlet passage of the main body, wherein a first valve assembly provided within the first valve chamber includes a first sealing member spring-biased to a seated position within the first valve chamber such that pressurized fluid provided at the fluid inlet passage of the main body at a pressure sufficient to overcome a force of said spring-bias of the first sealing member causes displacement of the first sealing member and flow of said pressurized fluid into the first valve chamber whereby fluid pressurization occurs within the interior space of the cannula cuff, wherein a second valve assembly provided within the second valve chamber includes a second sealing member spring-biased to a seated position within the second valve chamber to close a fluid inlet passage of the second valve chamber, wherein the fluid inlet passage of the second valve chamber is in fluid communication with the fluid outlet passage of the main body such that said fluid pressurization within the interior space of the cannula cuff causes displacement of the second sealing member proportional to a force of said spring-bias of the second sealing member, and wherein the second valve assembly includes a pressure level indicating portion that provides a visual indication of a level of said fluid pressurization within the interior space of the cannula cuff.

16. The tracheal breathing tube of claim 15 wherein the second valve chamber includes a pressure bleeding structure through which fluid from within the first valve chamber is released in response to the second sealing member being displaced from the seated position thereof when fluid pressure within the interior space of the cannula cuff is above a maximum cannula cuff pressure.

17. The tracheal breathing tube of claim 16 wherein:
the pressure bleeding structure includes one of a recess and an aperture exposed within a surface of the second valve chamber;
a leading edge of the pressure bleeding structure is located a first distance from an inlet of the second valve chamber; and
the sealing member of the second valve assembly and the second valve chamber are jointly configured whereby fluid pressure is maintained within the first valve chamber until the sealing member of the second valve assembly is displaced from the seated position by a distance equal to the first distance.

18. The tracheal breathing tube of claim 15 wherein:
the pressure level indicating portion includes a gauge member one of attached to and integral with the second sealing member;
the gauge member extends from the main body when the second sealing member is displaced from the seated position thereof; and
the gauge member extends from the main body by a prescribed maximum distance when a maximum cannula cuff pressure is exhibited at the fluid inlet passage of the second valve chamber.

* * * * *